(12) United States Patent
Ostroff et al.

(10) Patent No.: US 7,149,575 B2
(45) Date of Patent: Dec. 12, 2006

(54) SUBCUTANEOUS CARDIAC STIMULATOR DEVICE HAVING AN ANTERIORLY POSITIONED ELECTRODE

(75) Inventors: Alan H. Ostroff, San Clemente, CA (US); Paul Erlinger, San Clemente, CA (US); Gust H. Bardy, West Seattle, WA (US)

(73) Assignee: Cameron Health, Inc., San Clemente, CA (US)

( * ) Notice: Subject to any disclaimer, the term of this patent is extended or adjusted under 35 U.S.C. 154(b) by 500 days.

(21) Appl. No.: 10/150,434

(22) Filed: May 17, 2002

(65) Prior Publication Data

Related U.S. Application Data

(63) Continuation-in-part of application No. 10/011,956, filed on Nov. 5, 2001, which is a continuation-in-part of application No. 09/940,599, filed on Aug. 27, 2001, now Pat. No. 6,950,705, which is a continuation-in-part of application No. 09/663,607, filed on Sep. 18, 2000, now Pat. No. 6,721,597, and a continuation-in-part of application No. 09/663,606, filed on Sep. 18, 2000, now Pat. No. 6,647,292.

(51) Int. Cl.
*A61N 1/372* (2006.01)
*A61N 1/375* (2006.01)

(52) U.S. Cl. ............................................. 607/4; 607/9

(58) Field of Classification Search ................ 607/1–2, 607/4–5, 9, 36
See application file for complete search history.

(56) References Cited

U.S. PATENT DOCUMENTS

| | | | |
|---|---|---|---|
| 3,911,925 A | 10/1975 | Tillery | |
| 4,157,720 A | 6/1979 | Greatbatch | |
| 4,223,678 A | 9/1980 | Langer et al. | |
| 4,248,237 A | 2/1981 | Kenny | |
| 4,291,707 A | 9/1981 | Heilman et al. | |
| 4,314,095 A | 2/1982 | Moore et al. | |
| 4,402,322 A | 9/1983 | Duggan | |
| 4,407,288 A | 10/1983 | Langer et al. | |
| 4,424,818 A | 1/1984 | Doring et al. | |
| 4,567,900 A | 2/1986 | Moore | |
| 4,602,637 A | 7/1986 | Elmqvist et al. | |
| 4,603,705 A | 8/1986 | Speicher et al. | |
| 4,693,253 A | 9/1987 | Adams | |
| 4,765,341 A | 8/1988 | Mower et al. | |

(Continued)

FOREIGN PATENT DOCUMENTS

DE 298 01 807 U1 6/1998

(Continued)

OTHER PUBLICATIONS

International Search Report dated Mar. 26, 2002, PCT/US01/29168 filed Sep. 14, 2001, published as WO 02/22208 on Mar. 21, 2002, Subcutaneous Only Implantable Cardioverter Defibrlillator & Optional Pacer, Inventors: Gust H Bardy et al.

(Continued)

*Primary Examiner*—Robert E. Pezzuto
*Assistant Examiner*—Kristen Mullen
(74) *Attorney, Agent, or Firm*—Crompton, Seager & Tufte, LLC

(57) ABSTRACT

A subcutaneous cardiac device includes a subcutaneous electrode and a housing coupled to the subcutaneous electrode by a lead with a lead wire. The subcutaneous electrode is adapted to be implanted in a frontal region of the patient so as to overlap a portion of the patient's heart.

38 Claims, 12 Drawing Sheets

U.S. PATENT DOCUMENTS

| | | | |
|---|---|---|---|
| 4,800,883 A | 1/1989 | Winstrom | |
| 4,830,005 A | 5/1989 | Woskow | |
| 4,944,300 A | 7/1990 | Saksena | |
| 5,105,810 A | 4/1992 | Collins et al. | |
| 5,109,842 A | 5/1992 | Adinolfi | |
| 5,129,392 A | 7/1992 | Bardy et al. | |
| 5,133,353 A | 7/1992 | Hauser | |
| 5,184,616 A | 2/1993 | Weiss | |
| 5,203,348 A | 4/1993 | Dahl et al. | |
| 5,230,337 A | 7/1993 | Dahl et al. | |
| 5,241,960 A * | 9/1993 | Anderson et al. | 607/5 |
| 5,261,400 A | 11/1993 | Bardy | |
| 5,279,293 A * | 1/1994 | Andersen et al. | 607/5 |
| 5,300,106 A | 4/1994 | Dahl et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,376,103 A | 12/1994 | Anderson et al. | |
| 5,385,574 A | 1/1995 | Hauser et al. | |
| 5,391,200 A | 2/1995 | Kenknight et al. | |
| 5,411,539 A | 5/1995 | Neisz | |
| 5,411,547 A * | 5/1995 | Causey, III | 607/129 |
| 5,507,781 A | 4/1996 | Kroll et al. | |
| 5,509,923 A | 4/1996 | Pyka et al. | |
| 5,531,765 A | 7/1996 | Pless | |
| 5,531,766 A | 7/1996 | Kroll et al. | |
| 5,534,019 A | 7/1996 | Paspa | |
| 5,603,732 A | 2/1997 | Dahl et al. | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,325 A | 8/1997 | Augustine | |
| 5,690,648 A | 11/1997 | Howell et al. | |
| 5,697,953 A | 12/1997 | Kroll et al. | |
| 5,713,926 A | 2/1998 | Kenknight et al. | |
| 5,766,226 A | 6/1998 | Pedersen | |
| 5,776,169 A | 7/1998 | Schroeppel | |
| 5,843,132 A | 12/1998 | Ilvento | |
| 5,895,414 A | 4/1999 | Sanchez-Zambrano | |
| 5,919,211 A | 7/1999 | Adams | |
| 5,925,069 A | 7/1999 | Herber et al. | |
| 5,935,154 A | 8/1999 | Westlund | |
| 6,058,328 A | 5/2000 | Levine et al. | |
| 6,093,173 A | 7/2000 | Balceta et al. | |
| 6,144,879 A | 11/2000 | Gray | |
| 6,148,230 A * | 11/2000 | KenKnight | 600/516 |
| 6,241,751 B1 | 6/2001 | Morgan et al. | |
| 6,266,567 B1 | 7/2001 | Ishikawa et al. | |
| 6,280,462 B1 | 8/2001 | Hauser et al. | |

FOREIGN PATENT DOCUMENTS

| | | |
|---|---|---|
| EP | 0 095 727 A1 | 12/1983 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 A1 | 4/1993 |
| EP | 0 586 858 A1 | 3/1994 |
| EP | 0 627 237 A1 | 12/1994 |
| WO | WO 97/29802 A2 | 8/1997 |
| WO | WO 99/37362 A | 7/1999 |
| WO | WO 99/53991 A1 | 10/1999 |
| WO | WO 00/41766 B1 | 7/2000 |
| WO | WO 00/50120 A1 | 8/2000 |
| WO | WO 01/43649 A1 | 6/2001 |
| WO | WO 02/22208 A2 | 3/2002 |
| WO | WO 02/22208 A3 | 3/2002 |
| WO | WO 02/24275 A | 3/2002 |

OTHER PUBLICATIONS

Written Opinion dated Sep. 10, 2002, PCT/US01/29168 filed Sep. 14, 2001, published as WO 02/22208 on Mar. 21, 2002, Subcutaneous Only Implantable Cardioverter Defibrlillator & Optional Pacer. Inventors: Gust H Bardy et al.

International Search Report dated Mar. 21, 2002,, PCT/US01/29106 filed Sep. 14, 2001, published as WO 02/24275 on Mar. 28, 2002, Unitary Subcutaneous Only Implantable Cardioverter Defibrillator & Optional Pacer. Inventors: Gust H Bardy et al.

Written Opinion dated Sep. 3, 2002, PCT/US01/29106 filed Sep. 14, 2001, published as WO 02/24275 on Mar. 28, 2002, Unitary Subcutaneous Only Implantable Cardioverter Defibrillator & Optional Pacer Inventors: Gust H Bardy et al.

International Search Report dated Feb. 14, 2003, PCT/IB02/03452 filed Aug. 23, 2002; Not yet published; Applicant: Cameron Health Inc.

International Search Report dated Feb. 14, 2003, PCT/IB02/03453 filed Aug. 23, 2002; Not yet published; Applicant: Cameron Health Inc.

International Search Report dated Feb. 14, 2003, PCT/IB02/03467 filed Aug. 26, 2002; Not yet published; Applicant: Cameron Health Inc.

International Search Report dated Feb. 14, 2003, PCT/IB02/03469 filed Aug. 26, 2002; Not yet published; Applicant: Cameron Health Inc.

International Search Report dated Feb. 14, 2003, PCT/IB02/03484 filed Aug. 26, 2002; Not yet published; Applicant: Cameron Health Inc.

International Search Report dated Feb. 14, 2003, PCT/IB02/03488 filed Aug. 26, 2002; Not yet published; Applicant: Cameron Health Inc.

International Search Report dated Feb. 14, 2003, PCT/IB02/03522 filed Aug. 26, 2002; Not yet published; Applicant: Cameron Health Inc.

International Search Report dated Feb. 18, 2003, PCT/IB02/03503 filed Aug. 26, 2002; Not yet published; Applicant: Cameron Health Inc.

International Search Report dated Feb. 20, 2003, PCT/IB02/03447 filed Aug. 27, 2002; Not yet published; Applicant: Cameron Health Inc.

International Search Report dated Feb. 20, 2003, PCT/IB02/03481 filed Aug. 28, 2002; Not yet published; Applicant: Cameron Health Inc.

International Search Report dated Feb. 20, 2003, PCT/IB02/03501 filed Aug. 26, 2002; Not yet published; Applicant: Cameron Health Inc.

International Search Report dated Feb. 20, 2003, PCT/IB02/03502 filed Aug. 23, 2002; Not yet published; Applicant: Cameron Health Inc.

International Search Report dated Feb. 20, 2003, PCT/IB02/03525 filed Aug. 23, 2002; Not yet published; Applicant: Cameron Health Inc.

International Search Report dated Mar. 6, 2003, PCT/IB02/04513 filed Oct. 28, 2002; Not yet published; Applicant: Cameron Health Inc.

Office Action dated Oct. 15, 2002; U.S. Appl. No. 09/663,606; Inventors: Bardy et al; Copy of front page and Notice of References Cited by Examiner.

Office Action dated Nov. 5, 2001; U.S. Appl. No. 10/011,952; Inventors: Ostroff et al; Copy of front page and Notice of References Cited by Examiner.

Journal of the American Medical Association (JAMA), vol. 214, No. 6, 1123pp, Nov. 9, 1970, "Completely Implanted Defibrillator", an editorial comment by JC Schuder PhD.

Amer Soc Trans Artif Int Organs, vol. XVI, 1970, 207-212pp, "Experimental Ventricular Defibrillation With An Automatic & Completely Implanted System", by JC Schuder PhD et al.

Archives of Internal Medicine (Specialized Journal of the AMA), vol. 127, Feb. 1971, Letters to the Editor 317pp, "Standby Implanted Defibrillators", an editirial comment by JC Schuder Phd.

Journal of the American Medical Association (JAMA), vol. 213, 615-616pp, 1970, "Automatic Detection & Defibrillation of Lethal Arrhythmias—A New Concept", by Mirkowski et al.

IEEE Transactions on Bio-Medical Engineering, vol. BME-18, No. 6, Nov. 1971, 410-415pp, "Transthoracic Ventricular Defibrillation In The Dog With Truncated and Untruncated Exponential Stimuli" by JC Schuder PhD.et al.

PACE, vol. 16, Part 1, Jan. 1993, 95-124pp, "The Role Of An Engineering Oriented Medical Research Group in Developing Improved Methods & Devices For Achieving Ventricular Defibrillation: The University Of Missouri Experience", by JC Schuder Phd.

Journal of Cardiovascular Electrophysiology, vol. 12, No. 3, Mar. 2001, 356-360pp, Copyright 2001, by Future Publishing Company Inc, Armonk-NY 1050-0418,"Nonthoracotomy Implantable Cardioverter Defibrillator Placement In Children", by Rainer Gradaus MD et al.

Journal of Cardiovascular Electrophysiology, vol. 12, No. 3, Mar. 2001, 361-362pp, Copyright 2001, by Future Publishing Company Inc, Armonk-NY 1050-0418, "Implantable Defibrillators In Children: From Whence to Shock" by Richard A Friedman MD et al.

* cited by examiner

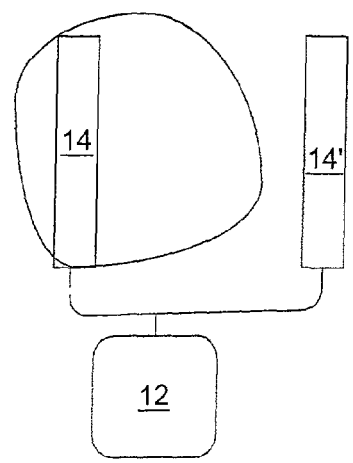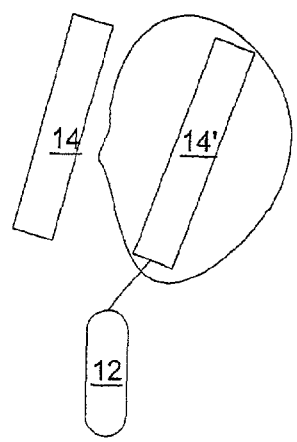
FIG. 4A　　　　　　　　FIG. 4B
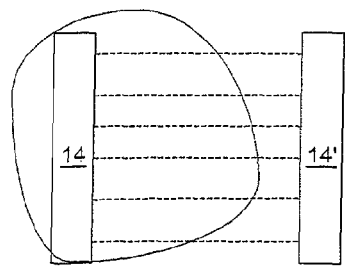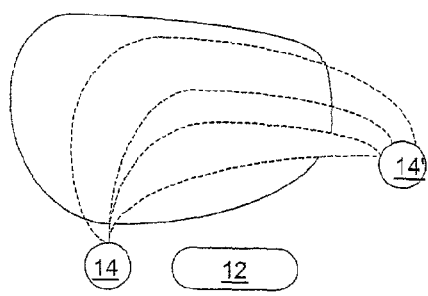
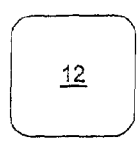
FIG. 4C　　　　　　　　FIG. 4D
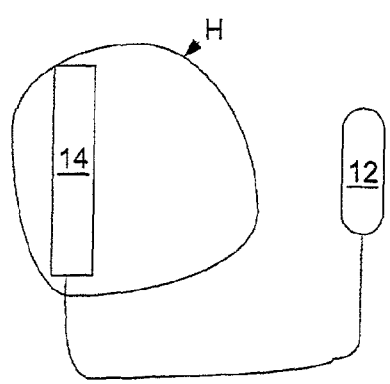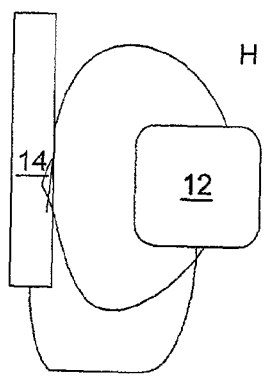
FIG. 5A　　　　　　　　FIG. 5B

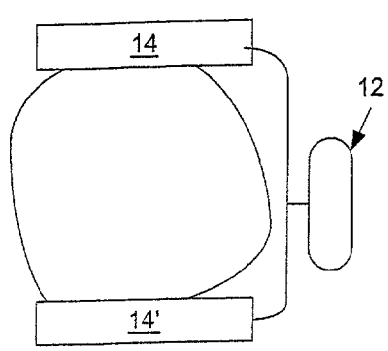
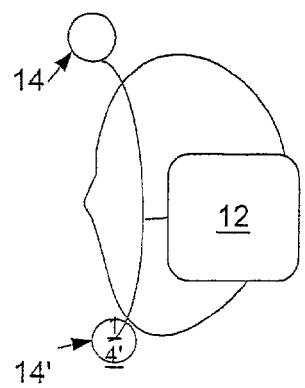
FIG. 6A  FIG. 6B
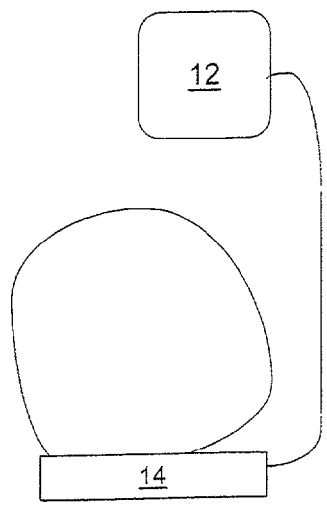
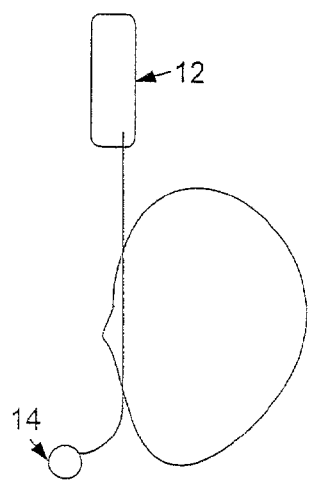
FIG. 7A  FIG. 7B
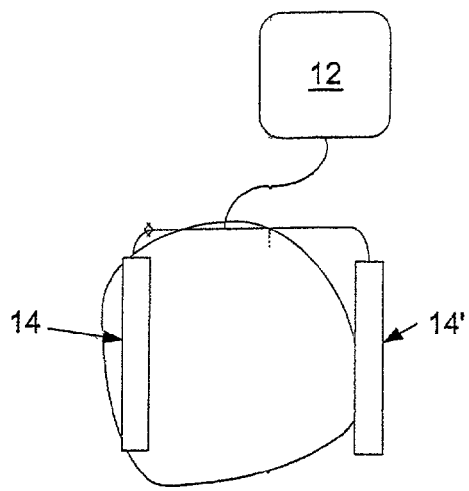
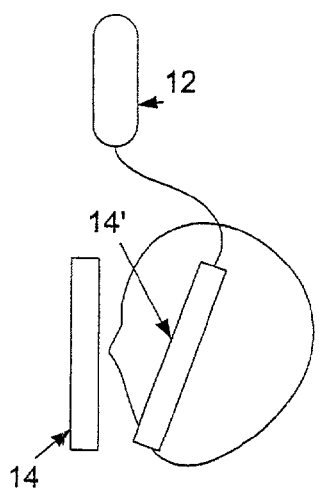
FIG. 8A  FIG. 8B

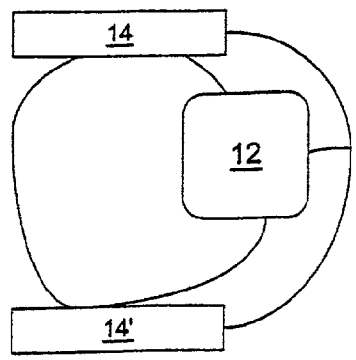
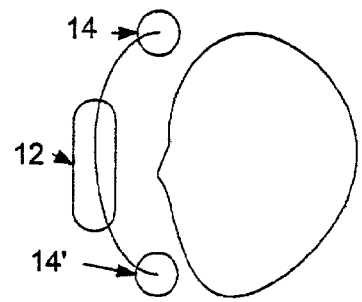
FIG. 9A
FIG. 9B
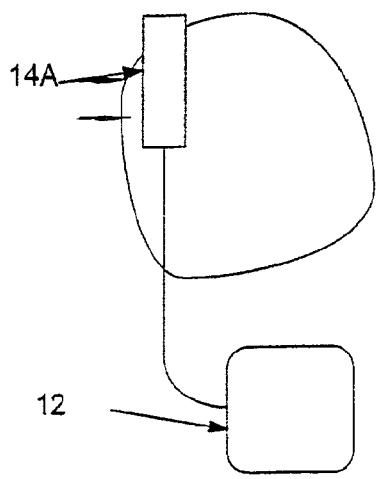
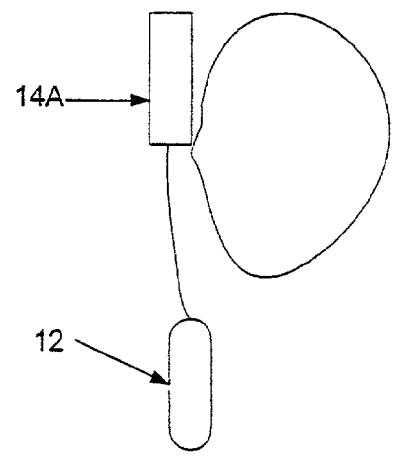
FIG. 10A
FIG. 10B
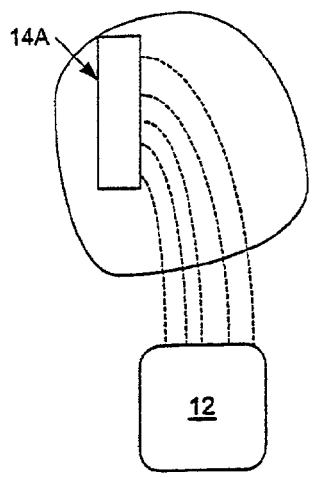
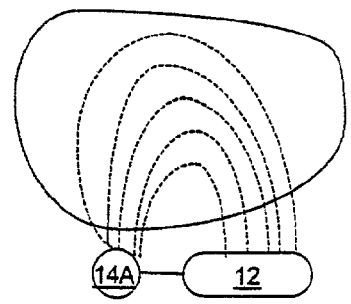
FIG. 10C
FIG. 10D

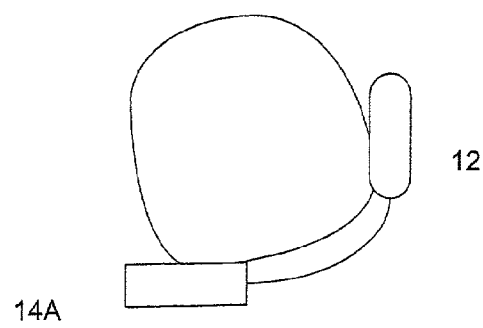
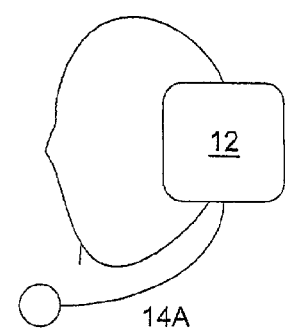
FIG. 11A
FIG. 11B
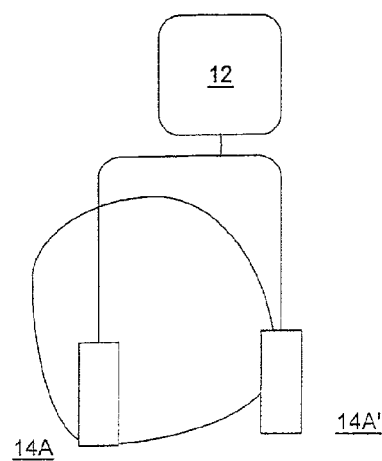
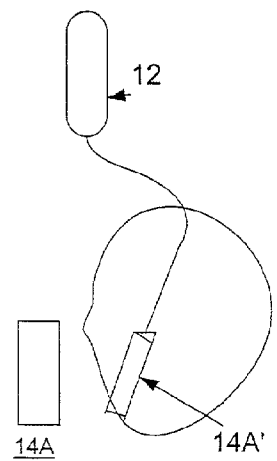
FIG. 12A
FIG. 12B
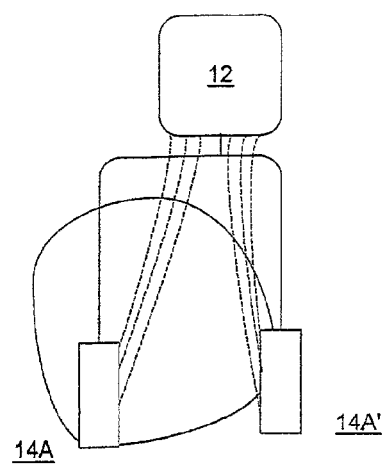
FIG. 12C

SUBCUTANEOUS CARDIAC STIMULATOR DEVICE HAVING AN ANTERIORLY POSITIONED ELECTRODE

RELATED APPLICATIONS

This application is a continuation-in-part of application Ser. No. 10/011,956, filed Nov. 5, 2001, which is a continuation-in-part of application Ser. No. 09/940,599, filed Aug. 27, 2001, now U.S. Pat. No. 6,950,705, which is a continuation-in-part of application Ser. No. 09/663,607, filed Sep. 18, 2000, now U.S. Pat. No. 6,721,597, and application Ser. No. 09/663,606, filed Sep. 18, 2000, now U.S. Pat. No. 6,647,292.

FIELD OF THE INVENTION

The present invention relates to a device and method for performing electrical cardiac stimulation, including: cardioversion, defibrillation and, optionally, pacing of the heart using subcutaneous electrodes. More specifically, the present invention relates to implantable cardioverter-defibrillator having at least one subcutaneous electrode, wherein the electrode is positioned generally in the frontal portion of the thorax, thereby creating a substantially uniform electric field across a patient's heart.

BACKGROUND OF THE INVENTION

The heart is a mechanical pump that is stimulated by electrical impulses. The mechanical action of the heart results in blood flow through a person's body. During a normal heartbeat, the right atrium (RA) of the heart fills with blood from veins within the body. The RA then contracts and blood is moved into the heart's right ventricle (RV). When the RV contracts, blood held within the RV is then pumped into the lungs. Blood returning from the lungs moves into the heart's left atrium (LA) and, after LA contraction, is pumped into the heart's left ventricle (LV). Finally, with the contraction of the left ventricle, blood from the LV is pumped throughout the body. Four heart valves keep the blood flowing in the proper directions during this process.

The electrical signal that drives the heart's mechanical contraction starts in the sino-atrial node (SA node). The SA node is a collection of specialized heart cells in the right atrium that automatically depolarize (change their potential). The depolarization wavefront that emanates from the SA node passes across all the cells of both atria and results in the heart's atrial contractions. When the advancing wavefront reaches the atrial-ventricular (AV node), it is delayed so that the contracting atria have time to fill the ventricles. The depolarizing wavefront then passes across the ventricles, causing them to contract and to pump blood to the lungs and body. This electrical activity occurs approximately 72 times a minute in a normal individual and is called normal sinus rhythm.

Abnormal electrical conditions can occur that can cause the heart to beat irregularly; these irregular beats are known as cardiac arrhythmias. Cardiac arrhythmias fall into two broad categories: slow heart beats or bradyarrhythmia and fast heart beats or tachyarrhythmia. These cardiac arrhythmias are clinically referred to as bradycardia and tachycardia, respectively.

Bradycardia often results from abnormal performance of the AV node. During a bradycardial event, stimuli generated by the heart's own natural pacemaker, the SA node, are improperly conducted to the rest of the heart's conduction system. As a result, other stimuli are generated, although their intrinsic rate is below the SA node's intrinsic rate. Clinical symptoms associated with bradycardia include lack of energy and dizziness, among others. These clinical symptoms arise as a result of the heart beating more slowly than usual.

Bradycardia has been treated for years with implantable pacemakers. Their primary function is to monitor the heart's intrinsic rhythm and to generate a stimulus strong enough to initiate a cardiac contraction in the absence of the heart's own intrinsic beat. Typically, these pacemakers operate in a demand mode in which the stimulus is applied only if the intrinsic rhythm is below a predetermined threshold.

Tachycardia often progresses to cardiac fibrillation, a condition in which synchronization of cell depolarizations is lost, and instead, there are chaotic, almost random electrical stimulations of the heart. Tachycardia often results from isehemic heart disease in which local myocardium performance is compromised and coordinated contraction of heart tissue is lost which leads to a loss of blood flow to the rest of the body. If fibrillation is left untreated, brain death can occur within several minutes, followed by complete death several minutes later.

Application of an electrical stimulus to a critical mass of cardiac tissue can be effective to cause the heart to recover from its chaotic condition and resume normal coordinated propagation of electrical stimulation wavefronts that result in the resumption of normal blood flow. Thus, the application of an electrical stimulus can revert a patient's heart to a sinus cardiac rhythm and the chambers of the heart once again act to pump in a coordinated fashion. This process is known as defibrillation.

Cardioversion/defibrillation is a technique employed to counter arrhythmic heart conditions including some tachycardias in the atria and/or ventricles. Typically, electrodes are employed to stimulate the heart with high energy electrical impulses or shocks, of a magnitude substantially greater than the intrinsic cardiac signals. The purpose of these high energy signals is to disrupt the generation of the chaotic cardiac signals and cause the heart to revert to a sinus rhythm.

There are two kinds of conventional cardioversion/defibrillation systems: internal cardioversion/defibrillation devices, or ICDs, and external automatic defibrillators, or AEDs. An ICD generally includes a housing containing a pulse generator, electrodes and leads connecting the electrodes to the housing. Traditionally, the electrodes of the ICD are implanted transvenously in the cardiac chambers, or alternatively, are attached to the external walls of the heart. Various structures of these types are disclosed in U.S. Pat. Nos. 4,603,705, 4,693,253, 4,944,300, 5,105,810, 4,567,900 and 5,618,287, all incorporated herein by reference.

In addition, U.S. Pat. Nos. 5,342,407 and 5,603,732, incorporated herein by reference, disclose an ICD with a pulse generator implanted in the abdomen and two electrodes. In one embodiment (FIG. 22), the two electrodes 188,190 are implanted subcutaneously and disposed in the thoracic region, outside of the ribs and on opposite sides of the heart. In another embodiment (FIG. 23), one electrode 206 is attached to the epicardial tissues and another electrode 200 is disposed inside the rib cage. In a third embodiment (FIG. 24), one electrode 208 is disposed away from the heart and the other electrode 210 is disposed inside the right ventricle. This system is very complicated and it is difficult to implant surgically.

Recently, some ICDs have been made with an electrode on the housing of the pulse generator, as illustrated in U.S.

Pat. Nos. 5,133,353, 5,261,400, 5,620,477, and 5,658,325, all incorporated herein by reference.

ICDs have proven to be very effective for treating various cardiac arrhythmias and are now an established therapy for the management of life threatening cardiac rhythms, such as ventricular fibrillation. However, commercially available ICDs have several disadvantages. First, commercially available ICDs must be implanted using somewhat complex and expensive surgical procedures that are performed by specially trained physicians. Moreover, lead placement procedures require special room equipped for fluoroscopy. These rooms are limited in number and therefore, limit the number of lead placement procedures, and ultimately the number of ICDs, that may be implanted in any given day.

Second, commercially available ICDs rely on transvenous leads for the placement of at least one electrode within the cardiac chambers. It has been found that over a period of time, transvenous lead electrodes may get dislodged from the cardiac tissues. Additionally, complications such as broken leads and undesirable tissue formations deposits on the electrodes are not uncommon. These problems are especially acute when leads carry two or more electrodes. Moreover, infection is a concern when implanting leads within a patient's vasculature.

Third, removing these ICDs and replacing them, if necessary, also requires complicated surgical procedures that may be more life-threatening than the initial implantation.

SUMMARY OF THE INVENTION

One embodiment of the present invention provides a subcutaneous cardiac stimulator device adapted to generate an electric field across the heart using at least one subcutaneous electrode positioned at a location selected to minimize the degree of surgical intervention.

In yet another embodiment, the present invention provides a subcutaneous cardiac stimulator device that does not include any leads extending into, or touching, a patient's heart or venous system. The electrodes can be positioned in a sternum position, a lateral position, an upper and/or a lower position with respect to the heart.

The present invention provides a device which, in one embodiment, has a curvilinear electrode that is positioned subcutaneously in the frontal or chest area of the body such that it overlaps a peripheral region of the heart. The term 'curvilinear electrode' is used herein to designate an electrode baying an elongated configuration with a substantially uniform cross-section along its length and having a cross-sectional diameter that is much smaller than its length by at least an order of magnitude.

The housing of the ICD device of the present invention can be active or inactive. If the housing is active, it is implanted in a position selected to generate an electric field with the electrode so that current passes through the heart and is effective to induce shocks therein. If the housing is inactive, then a separate electrode is also implanted subcutaneously and cooperates with the first electrode to generate the required electric field. Moreover, housing embodiments of the present invention can be implanted in a side position, an inframammary position or a pectoral position in the body.

BRIEF DESCRIPTION OF THE DRAWINGS

FIGS. 4A and 4B show a frontal and a side view of an inactive housing in the inframammary position with an electrode in the sternum and a second electrode in the lateral position;

FIGS. 4C and 4D show frontal view and a top view of the electrical field generated in the configuration of FIGS. 4A and 4B;

FIGS. 5A and 5B show a frontal view and a side view of an active housing in the side position and an electrode in the sternum position;

FIGS. 6A and 6B show a frontal view and a side view of an inactive housing in the side position and electrodes in the top and lower positions;

FIGS. 7A and 7B show a frontal view and a side view of an active housing in the pectoral position and an electrode in the lower position;

FIGS. 8A and 8B show a frontal view and a side view of an inactive housing in the pectoral position and electrodes in the sternum and lateral positions;

FIGS. 9A and 9B show a frontal view and a side view of an inactive housing on the right side of the heart and electrodes in the top and lower positions;

FIGS. 10A and 10B show a frontal view and a side view of an active housing in the inframammary position and an electrode in sternum position;

FIGS. 10C and 10D show a frontal and a top view of the electrical field generated by the configuration of FIGS. 10A and 10B;

FIGS. 11A and 11B show a frontal and a side view of an active housing in the side position and an electrode in the lower position;

FIGS. 12A and 12B show a frontal and a side view of an active housing and two electrodes in the sternum and lateral positions;

FIG. 12C shows the electrical field generated by one embodiment of the FIG. 12A configuration;

DETAILED DESCRIPTION OF THE INVENTION

Figure 1:
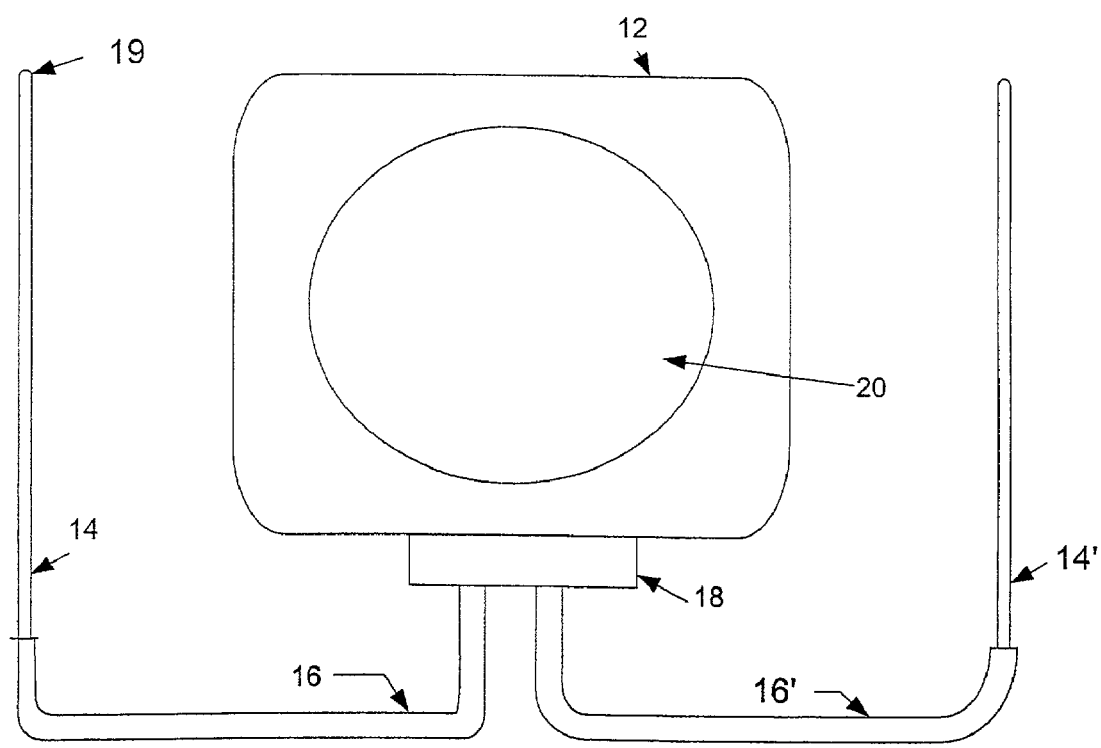
FIG. 1 shows a block diagram of a subcutaneous cardiac device having one or two subcutaneous electrodes constructed in accordance with this invention.

Referring now to the drawings, FIG. 1 shows an implantable cardiac device 10 constructed in accordance with one embodiment of the present invention. The device 10 includes a housing 12 containing a pulse generator (not shown), an electrode 14 and a lead 16. The electrode 14 is connected to the pulse generator through a header 18 disposed on the housing 12.

In particular embodiments of the present invention, the housing 12 can act as an active housing. In this embodiment, the housing 12 itself, comprises a second electrode for the ICD device 10. An active canister housing 12 is formed either with a continuously conductive surface, or with a separate conductive zone 20. The conductive surface or zone 20 of an active canister housing 12 is connected electrically to the circuitry disposed in the housing 12. If the whole housing 12 is used as an active electrode, then its surface area presents a low interface resistance with the patient's tissues, thereby lowering the losses in the tissue/electrode interface. In alternative embodiments, the housing 12 may be inactive, in which case the housing 12 is electrically isolated from its internal circuitry.

FIG. 1 further depicts a second electrode 14' that is connected to the header 18 by a second lead 16'. Particular embodiments of the present invention may utilize a second 16' or third (not shown) lead with optional electrode.

The housing 12 can be a conventional defibrillator housing used for programmable electronic circuitry that senses intrinsic cardiac activity and generates antiarrhythmic therapy (defibrillation shocks and/or pacing pulses) in the usual manner. To facilitate implantation, the circuitry, contained within the housing can also induce ventricular fibrillation for the purposes of resting the defibrillation threshold (DFT). DFT testing can be accomplished by delivering a shock during the vulnerable period of the cardiac cycle (T-wave) or by rapid pacing approximately 20 to 100 Hz for several seconds or by the application of direct current for several seconds or by the alternating current between 20 and 100 Hz for several seconds.

In particular embodiments, the housing 12 has a generally oval shape or a square shape with rounded corners. Although the housing 12 is illustrated as being square or rectangular, the housing 12 may also comprise any additional shapes conventionally known in the art. Moreover, the housing 12 is made of titanium and/or other similar biocompatible materials commonly used for implantable devices.

The housing 12 generally comprises a footprint in the range of 30–50 cm$^2$ and may be about 1.2 cm deep.

Electrode 14 is a subcutaneous electrode that is positioned under the skin and refrains from directly contacting the patient's heart. The subcutaneous electrode 14 may embody numerous shapes and sizes. For example, the electrode 14 may be planar, or may have a cross section of other shapes, e.g. circular. The electrode could be made from a coil, it could be braided or woven, or could be made by other similar means. In particular embodiments of the present invention, the electrode 14 is a curvilinear electrode. The term 'curvilinear electrode' is used herein to designate an electrode having an elongated rod-shaped configuration which could be straight or could be somewhat curved, and have a substantially uniform cross-section along its length and having a cross-sectional diameter that is much smaller than its length by at least an order of magnitude. Generally, the electrode 14 has a length of about 2–10 cm and a diameter of about 1–5 mm.

In electrodes 14 that are curvilinear, the tip of the electrode 14 may be rounded or formed with a dull point, as at 19 to assist its implantation. The electrode 14, or at least its outer surface, is made of an electrically conducting biocompatible material. The electrode 14 is preferably made of the titanium or stainless steel. Other electrode materials, conventionally known in the art, may additionally be used to form the electrode 14. In addition, particular electrode 14 embodiments may be coated with platinum or platinum alloy such as platinum iridium.

In general, the electrode 14 is flexible. Implanting a flexible electrode 14 minimizes discomfort associated with the implantation of the electrode 14 within the patient. In order to facilitate insertion of the electrode 14 within the patient, additional supporting mechanisms may be utilized during the insertion process. For example, a removable stylet may be used during the insertion process. After the electrode is properly positioned within the patient, the stylet is then removed from the electrode 14 (for example, from within the aperture formed from a coil electrode); rendering the electrode 14 flexible to conform to the patient's body for its duration. Additional insertion mechanisms, known in the art, may also be utilized to insert the flexible electrode 14. One insertion mechanism, for example, is the use of a peal away rigid sheath.

The electrode(s) and the housing 12 can be implanted using various configurations. While these configurations differ in the positioning of the electrode(s) and the housing 12, what they have in common is that least one electrode is disposed in the frontal or anterior region of the patient. The housing or the other electrode is then positioned so that it interfaces with the first electrode to generate an electrical field that passes through the heart and is effective to defibrillate the heart. In particular embodiments, the at least one electrode is disposed in the frontal or anterior region such that it overlaps a peripheral region of the heart as viewed from the front.

Figures 2A, 2B:
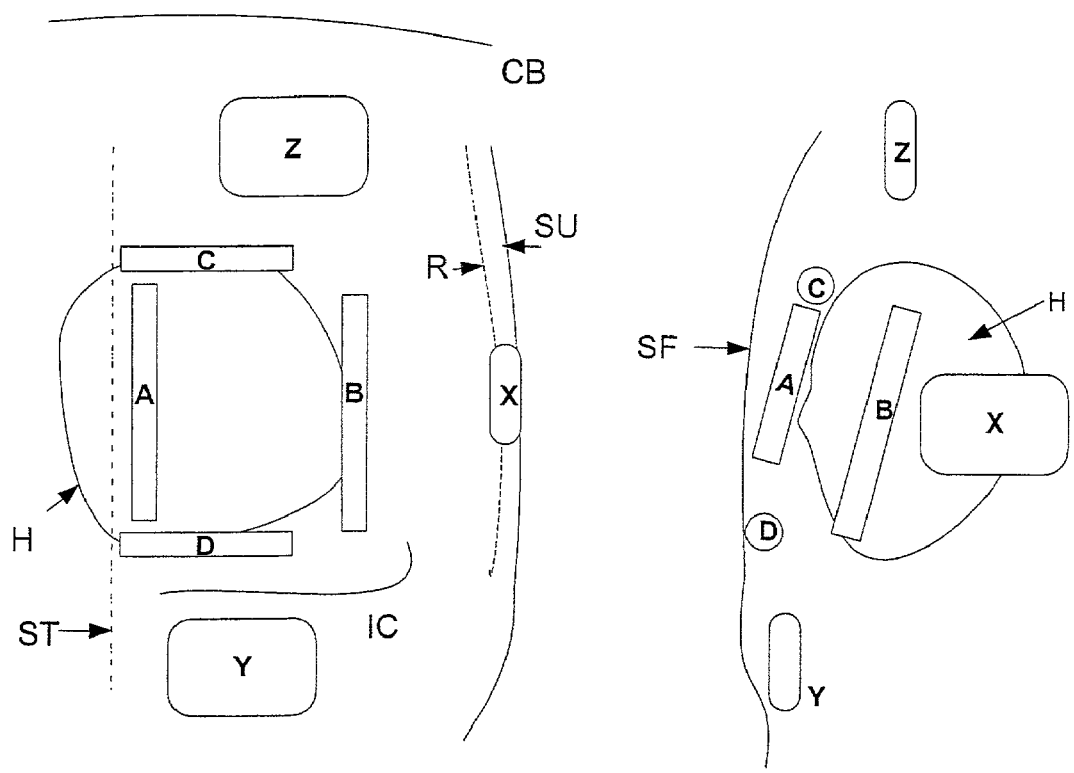
FIG. 2A is a diagrammatic view of the chest or frontal region of the patient with some of the possible electrode and housing positions in accordance with this invention.
FIG. 2B is a partial diagrammatic view of the side of the patient showing possible positions of the electrode and the housing.

Four electrode positions and three housing positions are identified in FIGS. 2A and 2B. In these figures, the heart is designated by the letter H, the sternum is indicated by an axis ST, the collar bone is indicated by a line CB and the inframammary crease is indicated by line IC. The lateral outline of the rib cage is indicated by line R and the skin extending outwardly from the rib cage laterally under the armpit is designated by the line SU, while the skin disposed in front of the rib cage is indicated by line SF. Obviously FIGS. 2A and 2B are not to scale, and the various tissues and bone structures shown therein are used to identify the relative locations of the electrode(s) 14, 14' and the housing 12 with respect to these physiological landmarks. The tunneling path used for the electrode placement is not necessary represented by the path indicated by the lead 16.

Four electrode positions are defined herein as positions A, B, C and D. As seen in the Figures, position A is a vertical position on the right side of the heart adjacent to the sternum. This position A is designated herein as the sternum position. Position B is disposed on the left side of the heart opposite from position A. Position B is also designated herein as the lateral position. Position C is a substantially horizontal position near the top of the heart and is designated herein as the upper position. Finally, position D is a substantially horizontal position near the bottom of the heart and is designated the lower position.

It is important to note that all four of these electrode positions are disposed subcutaneously, i.e., between the rib cage R and the skin SF in the frontal or anterior chest area.

Several of these electrodes positions are further depicted overlapping either the top, bottom, left or right peripheral region of the heart.

The tissues bounded by these four electrode positions are generally fatty tissues and/or comprise bony material—both having a relatively high electrical resistivity as compared to the resistivity of the cardiac tissues. Positioning the electrodes in the frontal or anterior chest area allow the naturally forming resistivity differential to better force electric current through the patient's heart, rather than shunting into surrounding tissue.

Because the electrode placement of the present invention refrains from accessing the vasculature of the patient, serious risks of infection are greatly reduced. Infections arising from the present invention would be more likely localized and easily treatable. Whereas, infections arising from prior art devices that utilize leads that access the patient's vasculature, tend to pose more serious risks to the patient's health.

In addition, positioning the electrodes in the frontal or anterior chest area eliminates the requirement of fluoroscopy. The use of fluoroscopy adds additional cost and risks to an ICD implantation procedure. Specifically, the physician must wear protective lead shielding and utilize specially designed electrophysiology laboratories equipped for fluoroscopy. Electrode placement in the present invention, however, follows predominant anatomical landmarks that are easily accessible, and are highly identifiable. Fluoroscopy, therefore, is not required because the ICD embodiments of the present invention are positioned in the subcutaneous frontal portion of the patient's chest, which is readily accessible to a physician without the need for fluoroscopy.

FIGS. 2A and 2B show three subcutaneous positions X, Y, Z for the housing 12. Position X is disposed on the left side of the rib cage, under the arm, and is designated herein as the side position. Position Y is a frontal position, under the inframammary crease IC and is designated herein as the inframammary position. Finally, position Z is also a frontal position and it corresponds to the conventional position for ICDs, above and to the left of heart under the collarbone CB. This position Z is designated herein as the pectoral position.

In the following discussion, the various configurations are now described with the housing being disposed at one of the locations X, Y or Z. Except as noted, for each housing position, two electrode configurations are disclosed: one for an active housing and a single electrode; and a second for an inactive housing, a first electrode and a second electrode.

Figure 3A:
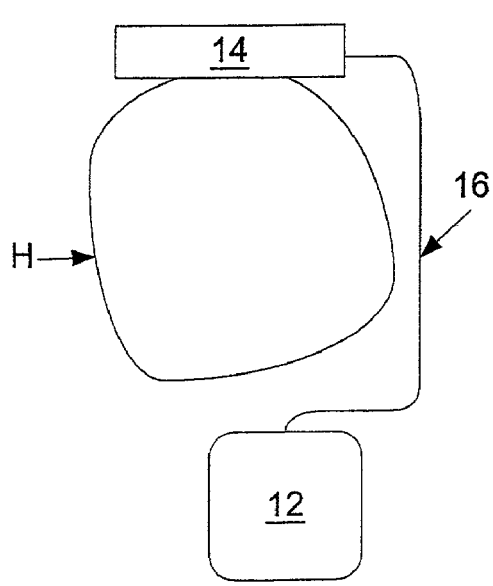
FIGS. 3A and 3B show a frontal view and a side view of an active housing in the inframammary position and an electrode in the upper position.
Figure 3B:
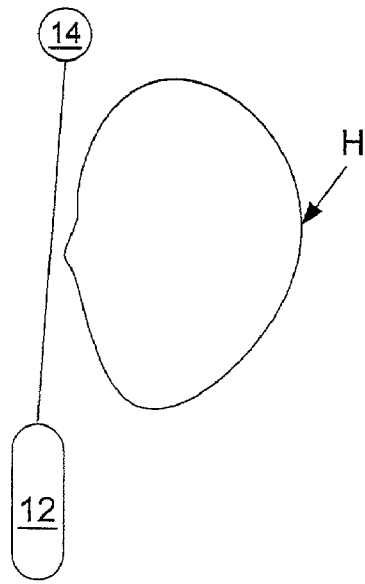

In FIGS. 3A and 3B, the housing 12 is an active housing and is shown implanted at position Y, or inframammary position. The electrode 14 is disposed horizontally in the upper position C. The lead 16 is threaded subcutaneously to the device. As illustrated in the Figures, the housing 12 and electrode 14 are both disposed outside the front portion of the rib cage, with the housing 12 being disposed below the heart H and the electrode 14 being disposed in the upper position at a level with the top portion of the heart H. Thus, in this embodiment, the housing 12 and the electrode 14 are positioned above and below the center of the heart C.

Figure 3C:
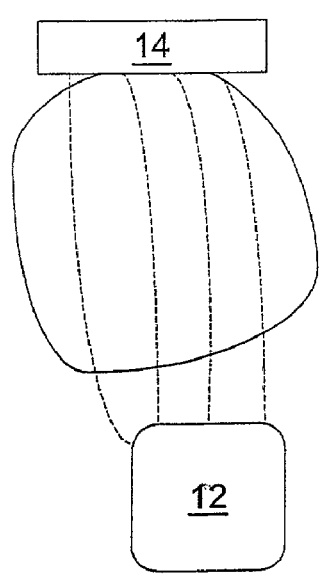
FIGS. 3C and 3D show the electrical field generated with the configuration of FIGS. 3A and 3B, respectively.
Figure 3D:
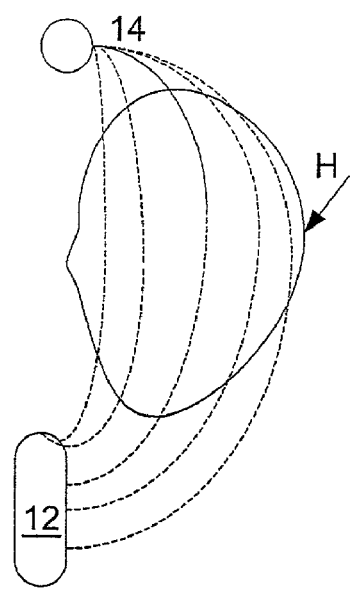

The tissues between the housing 12 and the electrode 14 are fatty tissues and/or bony material that have a much higher resistivity then that of the muscle between the ribs. Therefore, when a voltage is applied between the electrode 14 and the housing, current naturally follows the path of least resistance. In the position illustrated in FIGS. 3A and 3B, as with all the other embodiments depicted in the Figures herein, the applied voltage follows the lower conductivity of the heart muscle, and not the fat or bone. The electric field formed across the heart by this position is shown in detail in FIGS. 3C and 3D. Thus, the positions illustrated better direct a sufficient amount of current to be forced through the heart causing its defibrillation.

In FIGS. 4A and 4B, the housing 12 is an inactive housing shown implanted in the inframammary position Y and electrodes 14 and 14' are implanted in the sternum and lateral positions A and B, respectively. In this case, the electric field is established between the electrodes 14 and 14', as illustrated in FIGS. 4C and 4D. Again, because the tissues between the electrodes are fatty tissues and/or bony material, they have a higher resistivity then the cardiac tissues, and accordingly, electric current flows through the heart, rather than along a direct path between the two electrodes.

In FIGS. 5A and 5B, the housing 12 is an active housing implanted in the side position X and electrode 14 is in the sternum position A.

In FIGS. 6A and 6B, the housing 12 is an inactive housing implanted at the side position X and the electrodes 14, 14' are oriented horizontally at the upper and lower positions C and D, respectively.

In FIGS. 7A and 7B, the housing 12 is an active housing disposed at the pectoral position Z and electrode 14 is oriented horizontally at the lower position D.

In FIGS. 8A and 8B, the housing 12 is an inactive housing disposed at the pectoral position Z and electrodes 14 and 14' are arranged vertically at the sternum position A and lateral position B, respectively.

In FIGS. 9A and 9B, the housing 12 is inactive and is positioned above the heart, between the electrodes 14, 14' in positions C and D, respectively.

In the configurations described so far, an electric field is generated between a first electrode disposed horizontally or vertically along a front portion of the rib cage and either the housing or a second electrode disposed on an opposite side of the heart. However, other configurations may also be used in which the second electrode or housing is disposed along the front portion of the rib cage at a right angle with respect to a longitudinal axis of the first electrode. One such configuration is shown in FIGS. 10A and 10B. In this configuration, the first electrode 14A is disposed in the septum position A and the housing 12 is disposed in the inframammary position Y. As seen in FIGS. 10C and 10D (FIG. 10D being a top view), when a voltage is applied to between these two elements, an electric field is generated through the heart. However, the linear distance between the two elements generating the field has to be sufficiently large to insure that a substantial portion of the electric current passes through the heart and is not shunted directly between the first electrode and the housing. For this reason, the electrode in FIGS. 10A and 10B is shorter than the electrodes in the previous embodiments. For example, the electrode 14A may have half the length of the other electrodes 14, 14'. In addition, the electrode 14A is positioned as far as possible from the housing 12 while still being superimposed on a peripheral region of the heart.

FIGS. 11A and 11B show a configuration in which the active housing is in the side position X and the electrode 14A is in the lower position and has a shorter length.

In the following configurations, an active housing 12 is used with two short electrodes 14A, 14A', the two electrodes being shorted to each other so that the electric field is generated between each electrode and the housing.

In FIGS. 12A and 12B the active housing 12 is in pectoral position and the electrodes 14A, 14A' are in the sternum and lateral positions, respectively. In this configuration, the active housing 12 may generate an electric field with electrode 14A alone. Alternatively, the active housing 12 may generate an electric field with electrode 14A' alone. Finally, the active housing 12 may generate an electric field with both electrode 14A and electrode 14A'. The electric field created by such an arrangement is depicted in FIG. 12C. In this configuration, the electric field forms a broad wave front that traverses through the heart.

Figure 13A:
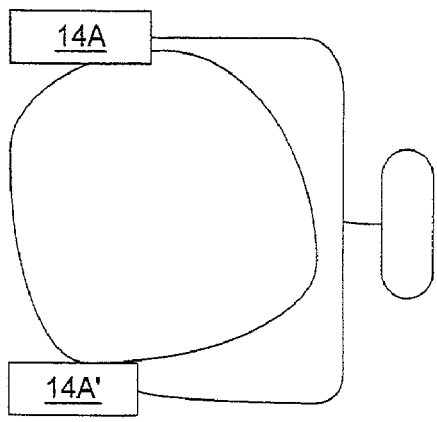
FIG. 13A shows a frontal view of an active housing in the side position with electrodes in the upper and lower positions.

In FIG. 13A the active housing is in the side position and the electrodes 14A and 14A' are in the upper and lower positions, respectively. Similar to FIG. 12A, the active housing 12 may generate at least three distinct electric fields—with electrode 14A alone, with electrode 14A' alone, and with both electrode 14A and electrode 14A'.

Figure 13B:
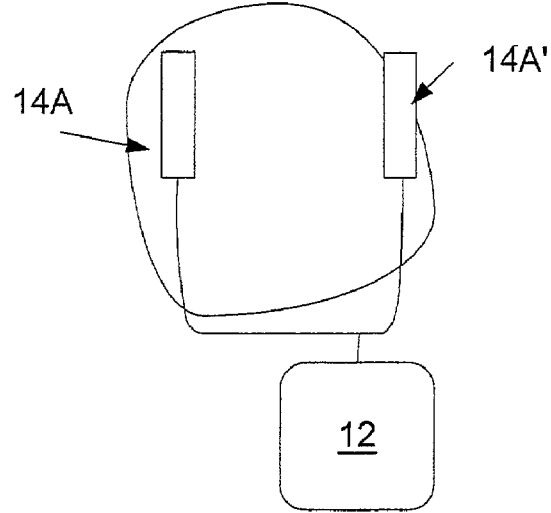
FIG. 13B shows a frontal view of an active housing in the inframammary position and electrodes in the sternum and lateral positions.

In FIG. 13B (which is a front view) the active housing is in the inframammary position and the electrodes 14A, 14A' are in the sternum and lateral positions, respectively.

In the following configurations, an electric field is generated between a first electrode disposed horizontally along a front portion of the rib cage and a housing disposed on the opposite side of the sternum. These embodiments describe a fifth and sixth electrode placement (C' and D', respectively). Moreover these embodiments encompass a fourth and fifth housing placement (Y' and Z', respectively).

Figure 14A:
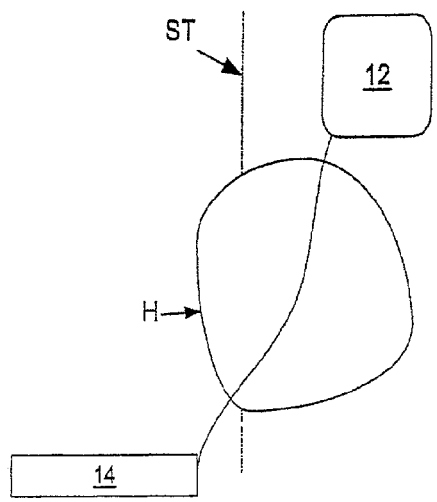
FIGS. 14A–14D show frontal view configuration of an active housing with an electrode positioned on either side of the sternum.

In FIG. 14A, the active housing 12 is in the pectoral position on the left side of the sternum (position Z), and the electrode 14 is in a substantially lower horizontal position on the right side of the sternum (position D').

Figure 14B:
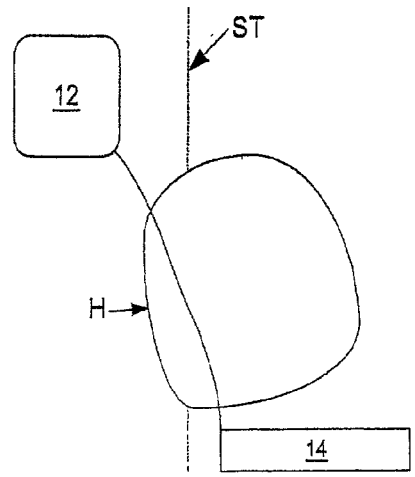

In FIG. 14B, the active housing 12 is in the pectoral position on the right side of the sternum (position Z'), and the electrode 14 is in the substantially lower horizontal position on the left side of the sternum (position D).

Figure 14C:
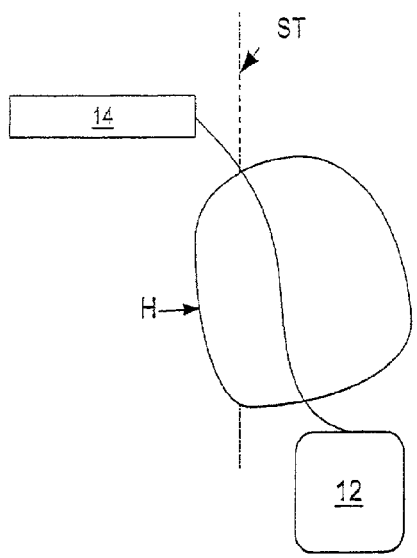

In FIG. 14C, the active housing 12 is in the inframammary position on the left side of the sternum (position Y), and the electrode 14 is in a substantially upper horizontal position on the right side of the sternum (position C').

Figure 14D:
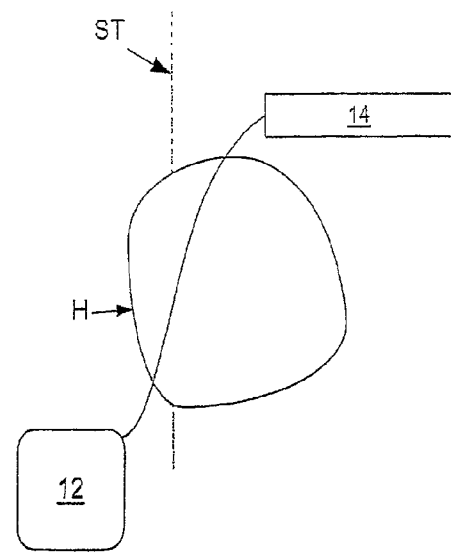

In FIG. 14D, the active housing 12 is in the inframammary position on the right side of the sternum (position Y'), and the electrode 14 is in a substantially upper horizontal position on the left side of the sternum (position C).

The cardiac device 10 can be used to apply defibrillation and pacing therapy. In the configuration shown in the Figures discussed so far, sensing can be effected by using the same elements that are used for defibrillation and/or pacing. Induction for DFT testing purposes can also use the same elements that are used for defibrillation and/or pacing.

Alternatively, separate electrodes can be provided for sensing and/or pacing. In one embodiment shown in FIG. 15A, a segmented electrode 30 is provided which can have approximately the same length as the electrode 14 in FIG. 1. The electrode 30 consists of three segments: an end electrode 32, an intermediate segment 34 made of a non-conductive material and a main electrode 36. The end electrode 32 can have a tip with a reduced diameter, similar to the tip 19 on electrode 14 in FIG. 1.

Preferably the three segments have substantially the same cross section so that the electrode 30 can be implanted easily in a tunnel in any of the electrode positions discussed above in a manner similar to electrode 14. The axial length of end electrode 32 can be up to 50% of the total length of the segmented electrode 30. The intermediate segment 34 can have a negligible axial dimension as long as it electrically isolates the end electrode 32 from the main electrode 36.

Figure 15A:
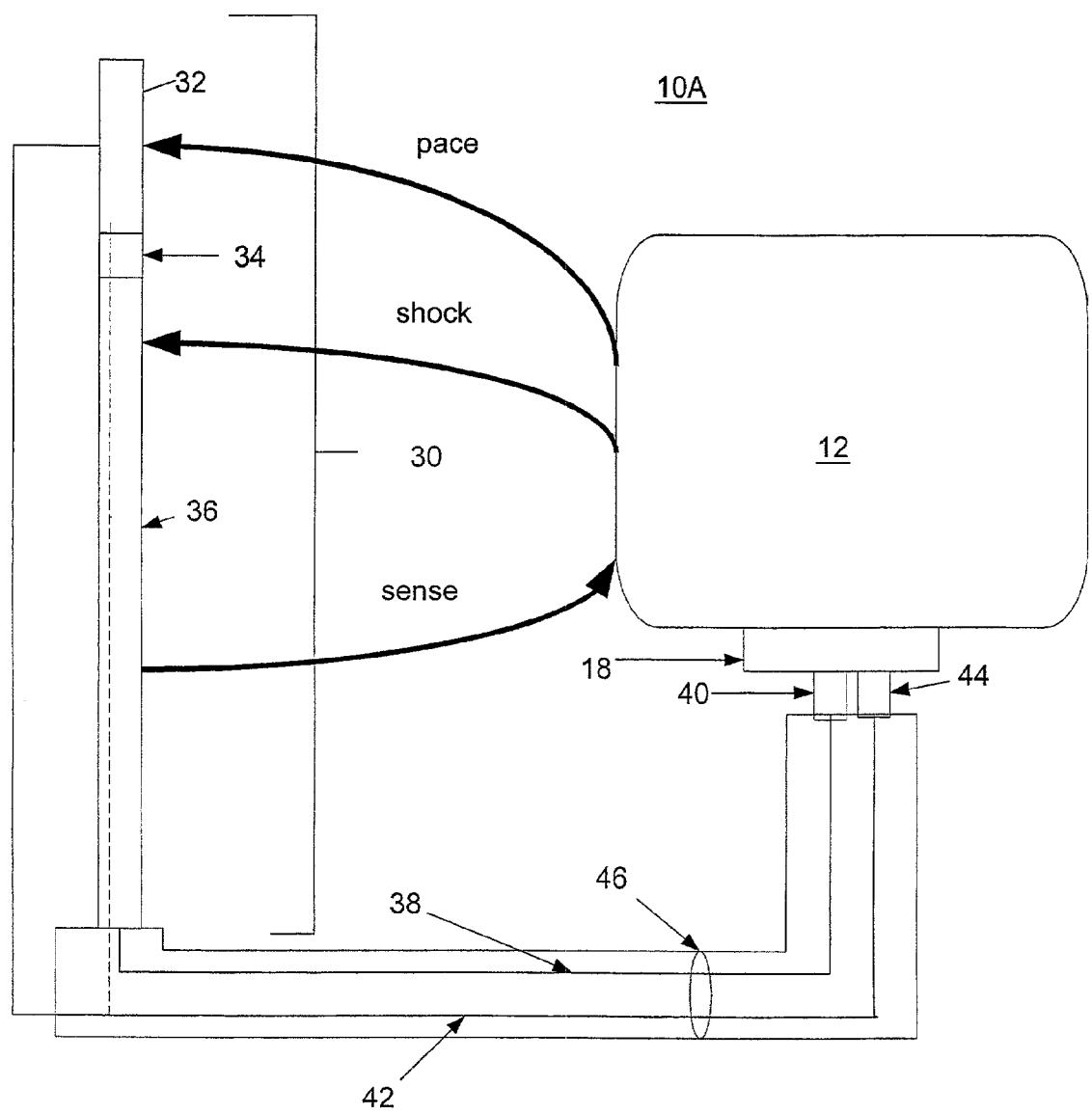
FIGS. 15A–15D show an active housing, a segmented electrode and various stimulations applied therebetween.

The main electrode 36 is connected to the housing 12 through a lead 38 and a connector 40 attached to the header. Similarly, segment 32 is connected by a lead 42 to header 18 through a connector 44. Alternatively, the two wires 38, 42 can be incorporated into a common lead 46. In this latter configuration, preferably, the segments 34, 36 are hollow to allow the wire 42 to pass therethrough and connect to the end electrode 32, as illustrated in FIG. 15A by the phantom line. Device 10A, shown in FIG. 15A, and incorporating electrode 30, housing 12 and lead 46 can be configured to operate in several modes. In one mode, shown in FIG. 15A, sensing and ventricular shocks can be applied between the main electrode 36 and the housing 12, while pacing can be applied between the end electrode 32 and the housing 12. This embodiment is particularly advantageous because it avoids stimulating the abdomen.

Figure 15B:
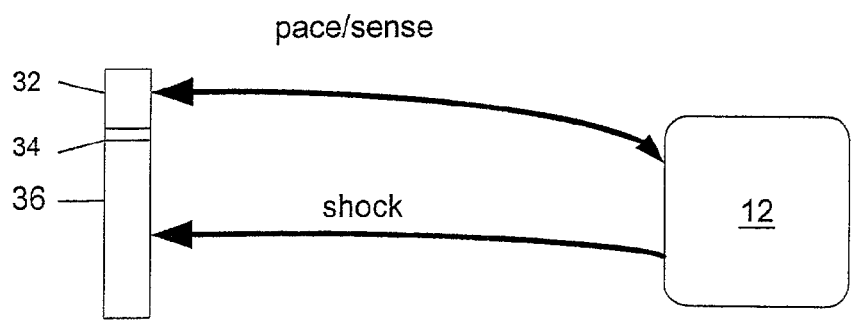
Figure 15C:
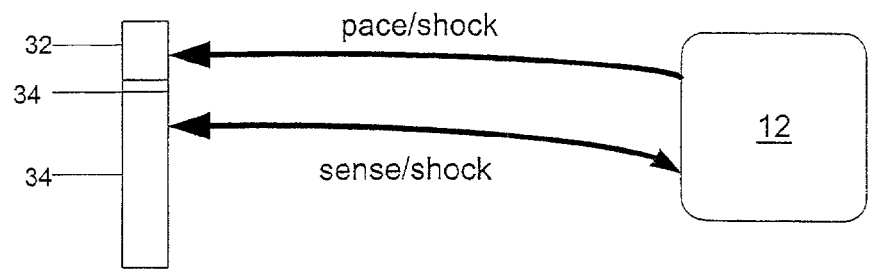
Figure 15D:
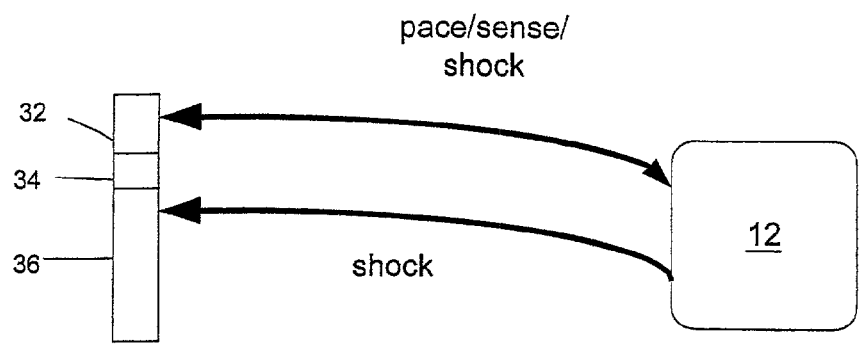

FIGS. 15B, 15C and 15D show other modes of operation. In FIG. 15B a mode is shown wherein pacing, sensing and induction are implemented between the end electrode and the housing and shock is applied between the main electrode and the housing. In FIG. 15C pacing and a shock can be applied between the end electrode 32 and the housing 12. Sensing is accomplished between the main electrode 36 and the housing 12. In addition, a shock can also be applied between the main electrode and the housing 12. Alternatively, during defibrillation the end and the main electrodes could be shorted and shock could be applied between both electrodes and the housing.

In FIG. 15D, pacing, sensing, induction and a shock is applied between the end electrode and the housing. A shock is additionally applied between the main electrode and the housing.

Figure 16:
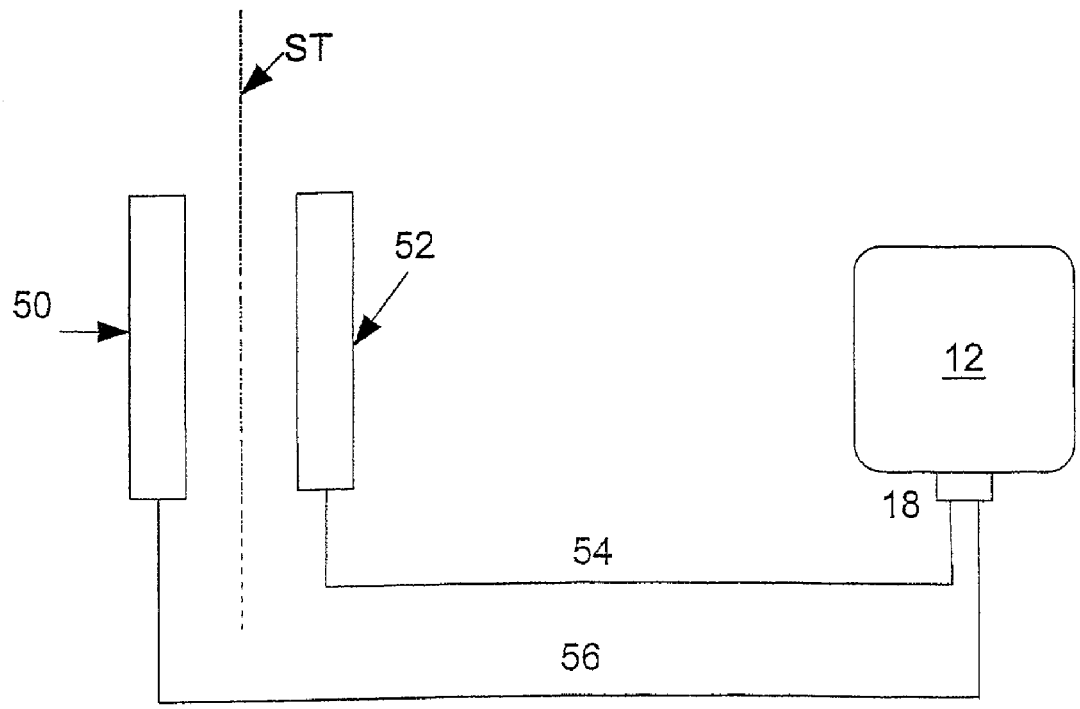
FIG. 16 shows an active housing and two electrodes disposed adjacent to the sternum.
Figure 17:
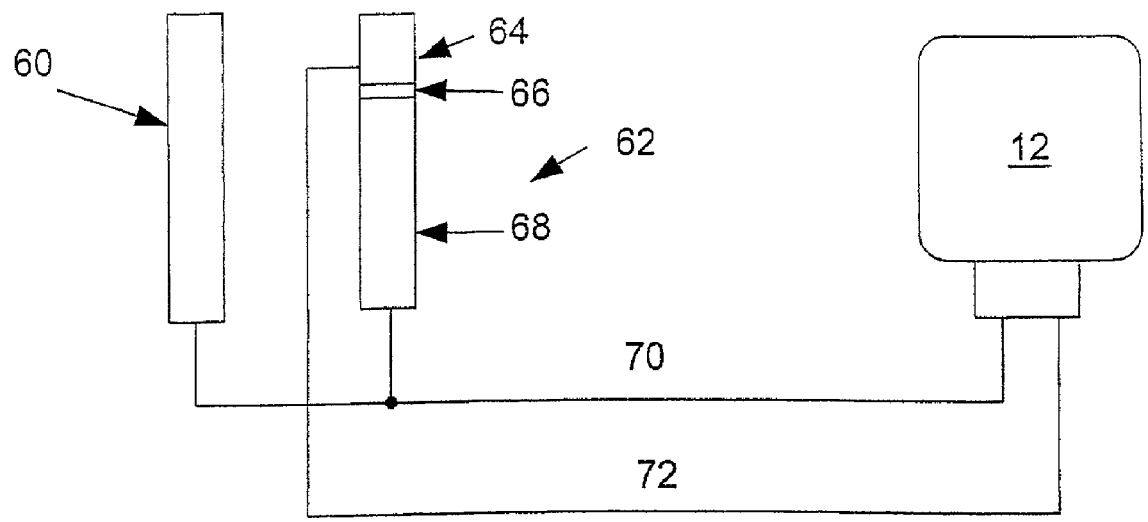
FIG. 17 shows an active housing and two electrodes disposed adjacent to the sternum, one of the electrodes being multi-segmented.

In the embodiments described so far, a single electrode element is envisioned that may be segmented but is disposed in a single tunnel at the various electrode positions. However, it may be advantageous in some instances to provide two electrode elements. FIG. 16 shows one multi-element electrode configuration. In this configuration, two electrode elements 50 and 52 are provided, each having a structure similar to electrode 14 or 14'. The electrode elements are adapted to be implanted parallel to each other. For example, the two elements can be implanted on either side of the sternum ST. In this configuration, each electrode element 50, 52 is provided with its own lead wire 54, 56 coupling the same to the housing 12 through a header 18 and a respective connector (not shown). The lead wires can be provided in a single lead, or in separate leads. Each of these electrode elements 50, 52 can be used for sensing, pacing, induction or shocks In another multi-electrode element embodiment shown, in FIG. 17, two electrode elements 60, 62 are provided. Electrode element 60 is similar to electrode 14 or 14' in FIG. 1 while electrode element 62 is multi-segmented, and thus it is similar to the electrode 30 of FIG. 16A. That is, electrode element 62 includes an end electrode 64, an intermediate segment 66 and a main electrode 68. Preferably, in this embodiment, electrode element 62 and the main electrode 68 are electrically connected to each other and connected to the housing 12 by a common lead wire 70, while end electrode 64 is connected to the housing by a second lead wire 72. Alternatively, the electrode element 62 could be connected to the end electrode 64. In addition, both elements 60, 62 could be segmented.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined in the language in which the appended claims are expressed.

We claim:

1. A method of implanting a cardiac device, the method comprising:
   implanting an electrode subcutaneously within a frontal region of a patient's chest; and
   implanting an active housing within the frontal region of the patient's chest, the housing and the subcutaneous electrode cooperating to provide selective antiarrhythmic, sensing and induction therapy between the housing and the subcutaneous electrode, wherein all electrodes are implanted subcutaneously.

2. The method of claim 1, wherein the subcutaneous electrode is positioned within the frontal region of the patient's chest such that is selected to overlap a peripheral region of a patient's heart.

3. The method of claim 1, wherein the subcutaneous electrode is substantially curvilinear in shape.

4. The method of claim 1, further comprising implanting a second subcutaneous electrode.

5. The method of claim 4, wherein the second subcutaneous electrode is positioned within the frontal region of the patient's chest.

6. The method of claim 4, wherein the second subcutaneous electrode is positioned within the lateral region of the patient's chest.

7. The method of claim 4, wherein the housing is active, further comprising applying selective antiarrhythmic, sensing and induction therapy between the subcutaneous electrode, the housing, and the second subcutaneous electrode.

8. The method of claim 4, wherein the housing is active, further providing selective antiarrhythmic, sensing and induction therapy between the subcutaneous electrode and the housing and selective antiarrhythmic, sensing and induction therapy between the second subcutaneous electrode and the housing.

9. The method of claim 4, wherein the subcutaneous electrode further comprises a first part and a second part, wherein the subcutaneous electrode senses intrinsic cardiac activity between the first subcutaneous electrode pan and the second subcutaneous electrode.

10. A method of implanting a cardiac device, the method comprising:
    implanting an electrode subcutaneously within a frontal region of a patient's chest; and
    implanting a housing within the frontal region of the patient's chest, the housing and the subcutaneous electrode cooperating to provide selective antiarrhythmic, sensing and induction therapy, wherein all electrodes are implanted subcutaneously;
    wherein the subcutaneous electrode further comprises a first part and a second part, wherein the subcutaneous electrode senses intrinsic cardiac activity between the first subcutaneous electrode part and the housing and applies shocks between the subcutaneous electrode and the housing.

11. The method of claim 10, wherein the subcutaneous electrode includes a first segment and a second segment, the first segment and the second segment being collinear.

12. The method of claim 10, wherein the subcutaneous electrode includes a first element and a second element, the first element and the second element being spaced from each other and substantially parallel.

13. A method of implanting a cardiac device, the method comprising:
    implanting an electrode subcutaneously within a frontal region of a patient's chest; and
    implanting a housing within the frontal region of the patient's chest, the housing and the subcutaneous electrode cooperating to provide selective antiarrhythmic, sensing and induction therapy, wherein all electrodes are implanted subcutaneously; wherein the subcutaneous electrode further comprises a first part and a second part, wherein the subcutaneous electrode senses intrinsic cardiac activity between the first subcutaneous electrode part and the second subcutaneous electrode part.

14. The method of claim 13, further comprising implanting a second subcutaneous electrode, wherein the housing is inactive, further comprising applying selective antiarrhythmic, sensing and induction therapy between the subcutaneous electrode and the second subcutaneous electrode.

15. A method of applying therapy to a patient's heart comprising:
    implanting at least a first electrode in a first subcutaneous electrode position within a patient's chest;
    implanting a housing within the patient's chest;
    selectively applying antiarrhythmic, sensing and induction therapy between the first subcutaneous electrode and the housing;
    wherein the first subcutaneous electrode position is disposed in a frontal region of the patient's chest, the first subcutaneous electrode position being selected from one of a sternum, a lateral, an upper and a lower position;
    wherein all electrodes are implanted subcutaneously.

16. The method of claim 15, wherein the housing is implanted in a position that is selected fern our of a side, an inframammary and a pectoral position.

17. The method of claim 15, wherein the first subcutaneous electrode position is selected on one side of the patient's heart and the housing position is selected on the other side of the heart in the frontal region of the patient.

18. The method of claim 15, wherein the first subcutaneous electrode position and the housing positions are selected perpendicular to each other.

19. The method of claim 15, the method further comprising implanting a second electrode in a second subcutaneous electrode position in the frontal region of the patient.

20. The method of claim 19, wherein the first subcutaneous electrode position and the second subcutaneous electrode position are selected on opposite sides of the patient's heart in the frontal region of the patient.

21. The method of claim 19, wherein selective antiarrhythmic, sensing and induction therapy is applied between the first electrode and the second electrode.

22. The method of claim 19, wherein selective antiarrhythmic, sensing and induction therapy is applied between the first electrode and the housing and selective antiarrhythmic, sensing and induction therapy is applied between the second electrode and the housing.

23. A method of implanting a cardiac device, the method comprising:
    implanting an electrode subcutaneously within a frontal region of a patient's chest, the subcutaneous electrode including a first part and a second part; and
    implanting an active housing within the frontal region of the patient's chest, the housing and the subcutaneous electrode cooperating to provide selective antiarrhythmic, sensing and induction therapy between the housing and the subcutaneous electrode, wherein the subcutaneous electrode senses intrinsic cardiac activity between the first subcutaneous electrode part and one of the housing or the second subcutaneous electrode part.

24. A cardiac device adapted to provide therapy to a patient with a frontal region defined in the chest area, said cardiac device comprising:
a subcutaneous electrode adapted to be disposed in the frontal region;
an active housing; and
a lead electrically coupling the subcutaneous electrode and the housing, wherein the subcutaneous electrode and active housing are adapted to generate an electrical field therebetween, the subcutaneous electrode and the housing configured to cooperate in providing selective antiarrhythmic, sensing and induction therapy between the housing and the subcutaneous electrode; wherein all electrodes are implanted subcutaneously.

25. The device of claim 24, wherein the subcutaneous electrode is adapted to be implanted in the frontal region of the patient's chest in a position selected to overlap a peripheral region of the heart.

26. The device of claim 24, wherein the subcutaneous electrode is adapted to be implanted in one of a sternum, a lateral, an upper and at lower position selected in the frontal region.

27. The device of claim 24, wherein the housing is adapted to be implanted in one of a side, an inframammary and a pectoral position.

28. The device of claim 24, further comprising a second subcutaneous electrode.

29. The device of claim 28, wherein the second subcutaneous electrode is configured to be positioned within the frontal region of the patient's chest.

30. The device of claim 28, wherein the second subcutaneous electrode is configured to be positioned within the lateral region of the patient's chest.

31. The device of claim 28, wherein the housing is active and wherein the subcutaneous electrode and the second subcutaneous electrode are configured to apply selective antiarrhythmic, sensing and induction therapy between the subcutaneous electrode and the second subcutaneous electrode.

32. The device of claim 28, wherein the housing and the second subcutaneous electrode are configured to apply selective antiarrhythmic, sensing and induction therapy between the second subcutaneous electrode and the housing.

33. The device of claim 28, wherein the subcutaneous electrode further comprises a first part and a second part, wherein the subcutaneous electrode senses intrinsic cardiac activity between the first subcutaneous electrode part and the second subcutaneous electrode.

34. A cardiac device adapted to provide therapy to a patient with a frontal region defined in the chest area, said cardiac device comprising:
a subcutaneous electrode adapted to be disposed in the frontal region;
a housing; and
a lead electrically coupling the subcutaneous electrode and the housing to generate an electrical field therebetween, the subcutaneous electrode and the housing providing selective antiarrhythmic, sensing and induction therapy; wherein all electrodes are implanted subcutaneously;
wherein the subcutaneous electrode further comprises a first part and a second part, wherein the subcutaneous electrode senses intrinsic cardiac activity between the first subcutaneous electrode part and the housing and applies shocks between the subcutaneous electrode and the housing.

35. The device of claim 34, wherein the subcutaneous electrode includes a first segment and a second segment, the first segment and the second segment being collinear.

36. The device of claim 34, wherein the subcutaneous electrode includes a first element and a second element, the first element and the second element being spaced from each other and substantially parallel.

37. A cardiac device adapted to provide therapy to a patient with a frontal region defined in the chest area, said cardiac device comprising:
a subcutaneous electrode adapted to be disposed in the frontal region;
a housing; and
a lead electrically coupling the subcutaneous electrode and the housing to generate an electrical field therebetween, the subcutaneous electrode and the housing providing selective antiarrhythmic, sensing and induction therapy; wherein all electrodes are implanted subcutaneously;
wherein the subcutaneous electrode further comprises a first part and a second part, wherein the subcutaneous electrode senses intrinsic cardiac activity between the first subcutaneous electrode part and the second subcutaneous electrode part.

38. The device of claim 37, further comprising a second subcutaneous electrode, wherein the housing is inactive and wherein the subcutaneous electrode and the second subcutaneous electrode are configured to apply selective antiarrhythmic, sensing and induction therapy between the subcutaneous electrode and the second subcutaneous electrode.

* * * * *

UNITED STATES PATENT AND TRADEMARK OFFICE
CERTIFICATE OF CORRECTION

PATENT NO. : 7,149,575 B2  
APPLICATION NO. : 10/150434  
DATED : December 12, 2006  
INVENTOR(S) : Alan H. Ostroff et al.

It is certified that error appears in the above-identified patent and that said Letters Patent is hereby corrected as shown below:

Column 2  
Line 18, delete "isehemic" and insert therefor -- ischemic --.

Column 3  
Line 47, delete "baying" and insert therefor -- having --.

Column 5  
Line 35, delete "resting" and insert therefor -- testing --.

Column 11  
Line 39, delete "pan" and insert therefor -- part --.

Column 12  
Line 31, delete "fern our" and insert therefor -- from one --.

Column 13  
Line 24, delete "at" and insert therefor -- a --.

Signed and Sealed this

Fifteenth Day of May, 2007

JON W. DUDAS  
*Director of the United States Patent and Trademark Office*